United States Patent
Tanner et al.

(10) Patent No.: US 7,711,431 B2
(45) Date of Patent: May 4, 2010

(54) METHOD AND DEVICE FOR STIMULATING THE BRAIN

(75) Inventors: Philip Tanner, Munich (DE); Thomas Bauch, Munich (DE)

(73) Assignee: BrainLAB AG, Feldkirchen (DE)

( * ) Notice: Subject to any disclaimer, the term of this patent is extended or adjusted under 35 U.S.C. 154(b) by 917 days.

(21) Appl. No.: 10/910,043

(22) Filed: Aug. 3, 2004

(65) Prior Publication Data
US 2005/0033380 A1 Feb. 10, 2005

Related U.S. Application Data

(60) Provisional application No. 60/506,030, filed on Sep. 25, 2003.

(30) Foreign Application Priority Data
Aug. 4, 2003 (EP) .................................. 03016697

(51) Int. Cl.
*A61N 1/08* (2006.01)
(52) U.S. Cl. ............................................ 607/45; 600/9
(58) Field of Classification Search ................ 600/373, 600/378, 544, 9–15; 607/2, 45, 115
See application file for complete search history.

(56) References Cited

U.S. PATENT DOCUMENTS

| 4,407,299 A | * | 10/1983 | Culver .......................... 600/544 |
| 5,331,970 A | * | 7/1994 | Gevins et al. ................ 600/544 |
| 6,463,328 B1 | * | 10/2002 | John ............................ 607/45 |
| 7,239,910 B2 | * | 7/2007 | Tanner ......................... 600/544 |
| 2003/0004392 A1 | | 1/2003 | Tanner et al. |
| 2003/0023159 A1 | | 1/2003 | Tanner |
| 2003/0050527 A1 | | 3/2003 | Fox et al. |
| 2005/0113630 A1 | * | 5/2005 | Fox et al. ..................... 600/13 |

FOREIGN PATENT DOCUMENTS

WO 02/073526 9/2002

OTHER PUBLICATIONS

Webster's Ninth New Collegiate Dictionary (Springfiled, Massachsuetts, U.S.A.: Merriam-Webster, Inc. Publishers, 1990),196.*
Henry Gray, Anatomy, Descriptive and Surgical (New Youk; Bounty Books, 1977, 678-680.*

* cited by examiner

*Primary Examiner*—Carl H Layno
*Assistant Examiner*—Frances P Oropeza
(74) *Attorney, Agent, or Firm*—Renner, Otto, Boisselle & Sklar, LLP

(57) ABSTRACT

A method for stimulating a particular area of a brain using a stimulation device includes detecting a spatial structure of a head and determining electrical and/or magnetic properties of at least one part of anatomical structures of the head. An energy amount to be provided by the stimulation device for stimulating the particular area of the brain is calculated automatically based on the spatial structure of the head and the determined electrical and/or magnetic properties of at least one part of the anatomical structures of the head.

22 Claims, 3 Drawing Sheets

METHOD AND DEVICE FOR STIMULATING THE BRAIN

RELATED APPLICATION DATA

This application claims priority of European Patent Application No. EP 03 0160 697.6 filed Aug. 4, 2003, and U.S. Provisional Application No. 60/506,030, filed on Sep. 25, 2003, which are incorporated herein by reference in its entirety.

FIELD OF THE INVENTION

The invention relates generally to a method and device for stimulating the brain and, more particularly, to a method and device for transcranial magnetic stimulation (TMS) of a particular area of the brain.

In various areas of medicine, such as neurology, psychiatry or brain surgery, it is desirable to be able to localize particular functional areas of the brain in order, for example, to be able to map brain functions. If, for example, a brain tumor is to be removed by surgery, then, as far as possible, the tumor should be removed without, if possible, damaging so-called primary areas of the brain that play a decisive role in a person's motor and sensory systems, language or visual capabilities. Surgery should, if possible, avoid damaging these areas at all, or only to an exceedingly small extent.

In accordance with a known direct method, such specific areas of the brain have been located intra-operatively by direct cortical stimulation (DCS) on an exposed cranium using electrodes. In this process, an electrode can be inserted into a particular area of the brain and an electrical impulse applied, wherein the reaction of the person being examined following the electrical impulse, for example, the twitching of a muscle or the perception of visual impressions, can be observed. The specific areas of the brain located by direct cortical stimulation can be marked using small, attached plates that help the surgeon's orientation in a subsequent brain operation with respect to the areas of the brain that are, as far as possible, not to be damaged. To date, direct cortical stimulation represents the most precise method for mapping brain functions, enabling accuracy in the range of a few millimeters when locating particular areas of the brain. However, this method can only be performed intra-operatively with the person under examination having to be fully conscious. This, however, can lead to problems in the application of this method, since this is an unpleasant state for the person being examined and, if complications arise, the person cannot simply be laid down and made to relax, due to the exposed cranium.

Furthermore, various indirect methods are known for mapping brain functions. However, these can only achieve considerably lower accuracy in locating specific areas of the brain. Thus, in functional nuclear spin tomography (fMRI), for example, a person being examined has to perform particular actions, such as a sweep of the hand, which promotes blood flow to the areas of the brain assigned to these actions. This change in the blood flow in particular areas of the brain may be measured during neuronal activity due to the decoupling of blood flow and oxygen consumption, since this gives rise to hyperoxygenation and, thus, a drop in the concentration of paramagnetic deoxyhaemoglobin (BOLD effect), which may then be measured as a so-called "endogenic contrast medium" using suitable sequences and nuclear spin tomography. However, as mentioned above, this method is relatively imprecise and only provides spatial resolution in the range of about 0.5 to 1.0 cm.

A method is known from Neurosurgery 1992-1998, December 1997, Volume 41, Number 6, 1319 "Stereotactic Transcranial Magnetic Stimulation: Correlation with Direct Electrical Cortical Stimulation", wherein stereotactic transcranial magnetic stimulation (TMS) is used for pre-operative functional mapping of the motor cortex. In this process, a patient's head is connected firmly and immovably to a headrest provided with a rotating arm on which a figure-eight coil is arranged, such that the tip of the arm lies beneath the intersecting point of the coil. In this way, the arm is aligned such that the tip lying beneath the intersecting point of the two coils points to a particular area in which a current is to be induced.

A method is known from U.S. Pat. No. 5,738,625 for magnetically stimulating nerve cells.

U.S. Pat. No. 5,644,234 describes a nuclear spin resonance (MR) method in which the position of a micro-coil in an object is to be determined.

A method and a device for transcranial magnetic stimulation of the brain are known from WO 98/06342, in which a broadly hemispherical magnetic core wound with coils is used to generate a stimulation signal. The described device and method are intended to localize the speech function.

Methods and a device for transcranial magnetic stimulation to non-invasively localize particular areas of the brain are known from commonly owned EP 1 273 320 A1 and corresponding U.S. Patent Pub. App. No 2003/0004392A1, which is incorporated herein by reference in its entirety (including its disclosure with respect to stimulating areas of the brain and in particular with respect to generating simulation models).

Furthermore, methods and devices for non-invasively localizing and/or describing the function of particular areas of the brain, such as primary or secondary areas of the brain, for mapping brain functions are known from the European patent applications having the application numbers 02 002 032.7 and 02 002 033.5.

SUMMARY OF THE INVENTION

In accordance with one aspect of the invention, the invention is directed to a method and device for stimulating particular areas of a brain, using which the precision of stimulating a particular area can be improved. In accordance with another aspect, the invention is directed to a method and device for more simply localizing areas of the brain.

It is to be appreciated that "stimulation," as used herein, includes not only actually, actively stimulating a particular area or point of the brain, but also applying or generating signals, which cause certain areas of the brain to be functionally suppressed, often also referred to as functional lesion. The term "stimulate" is accordingly to be understood such that certain stimulation signals can also cause brain functions to be blocked or inhibited. An area of the brain can be stimulated or inhibited by applying or generating signals in the brain using a stimulation device, such as a coil attached to the head, through which current flows, in order, by induction, to generate electrical signals in the brain, wherein the signals can be a particular impulse form or a succession of impulses having particular impulse forms and one or more predetermined frequencies. It has been shown that certain areas of the brain can be blocked or inhibited using higher frequencies, for example, in the range of 50 Hz, such that the functions to be fulfilled by the areas of the brain affected, such as perceiving an external stimulus, can no longer be performed. In this respect, the areas of the brain are preferably stimulated using a single magnetic or magnetically induced electrical impulse.

In accordance with one embodiment, the method for stimulating a particular area of a brain using a stimulation device, such as an induction coil, includes recording the spatial structure of the head. This can be done using, for example, a nuclear spin resonance method (MRI), computer tomography (CT), an ultrasound method or another suitable method, in order to obtain data for defining at least a part of the anatomical structure of the head, such as the position, nature and/or thickness of bones and the position and type or also thickness of tissue, such as the scalp or dura mater.

Particular properties of the anatomical structure(s) of the head, such as layers over the head and also the position and structure of the brain in the head, can be determined from the spatial structure of at least a part of the head, determined in this way. From this data, it is possible to calculate, (in one embodiment, automatically) how large an energy amount has to be in order to guide a stimulation or induction device, so that a particular area of the brain can be stimulated as precisely as possible. Thus, a magnetic field generated by an induction device can be set, and its field strength fixed, such that a desired area on or in the brain can be stimulated as precisely as possible using a settable current induced therein. For example, the dielectric properties of tissue and bone structures lying above the area to be stimulated can be taken into account for setting the magnetic field and/or fixing the energy amount for the induction device.

In the past, the energy amount and/or magnetic field have been set manually on the basis of estimated values. However, the methodology described herein enables a particular energy amount to be precisely focused onto a particular defined area on the surface of the brain or at a particular depth below the surface in the interior of the brain, which enables even a small defined area to be precisely stimulated.

It is to be appreciated that transcranial magnetic stimulation of a particular area of the brain can thus be improved, and, in particular, made more precise. This enables specific areas of the brain, for example, the aforementioned primary areas of the brain, to be precisely and non-invasively localized, such that pre-operative surgical planning can be improved. Furthermore, the method described herein can also be used to examine or cure other brain dysfunctions, such as for diagnosing epilepsy or Parkinson's disease. In this way, the method described herein enables the mapping of brain functions without having to open a person's cranium in order to be able to access the brain directly.

In one embodiment, the thickness and/or type or nature of bones and/or tissue are determined, as properties of anatomical structures or structures in the head, using suitable recording methods, such as computer tomography, for determining the bone type and structure or nuclear spin resonance methods for determining the tissue types or structure. Methods for recording body structures and for assigning various recordings to each other are known from the prior art and will not be described in detail herein.

In one embodiment, the head is modeled based on the properties of anatomical structures or layers in the head, determined using suitable methods. For example a finite multiple-shell model, such as a three-shell model, of the head can be produced, such that the distribution of electrical and/or magnetic fields in the head or on or in particular areas of the brain can be calculated using, for example, finite element methods. With respect to generating a simulation model of the head, reference is made to EP 1 273 320 A1 and corresponding U.S. Patent Pub. App. No 2003/0004392A1, the disclosure of which is incorporated herein by reference in its entirety. Alternatively, a simulation model of the induction device used for stimulating can be produced. On the basis of the simulation model of the head, and optionally also the stimulation device, it is possible to determine how large the energy amount to be supplied to the stimulation device has to be, when a particular area of the brain is to be stimulated.

In one preferred embodiment, markers, such as passive markers, are arranged on the head and/or on the induction device, in order to be able to track the induction device and/or the head. Referencing and tracking persons and/or instruments is known from the prior art and will not be described here in more detail. The induction device and head are matched so as to be able to define the relative spatial position of the induction device and the head as precisely as possible. One advantage of using markers is that a person being examined does not have to be positioned spatially fixed, but rather that particular areas of the brain can still be precisely stimulated, even if a person moves freely around in space.

Tracking the induction device or TMS coil together with the head enables the energy amount, which is supplied to the induction device in order to generate a magnetic field necessary for stimulating an area of the brain, to be automatically set or corrected. Accordingly, the induction device can be moved over the head and the energy supplied to the induction device can be set depending on the relative position of the induction device and the head, such that only the desired area of the brain is stimulated by a magnetic field generated by the induction device. If, for example, the induction device and the head are situated in a relative positional relationship, which does not enable the desired area of the brain to be stimulated, then the energy supply to the induction device can be interrupted.

In one embodiment, the energy amount supplied to the induction device can be set depending on the area of the brain to be stimulated or inhibited, respectively, such that the energy amount supplied to the induction device can be set depending on the generally known function of an area of the brain, such as the visual, auditory or motor cortex. In one embodiment, in can be advantageous to determine the depth, below the surface of the brain or head, of an area of the brain to be stimulated in order to optimally set the energy amount supplied to the induction device.

The stimulation or induction device can include at least one coil, for example, in the form of an 8, to which electrical impulses can be applied.

An area of the brain can be stimulated by electrical impulses applied to the stimulation or induction device, which can have a build-up time in the range of 1 μs to 1 ms and a duration of 10 μs to 1000 μs. In this way, the individual impulses can be applied with a periodic pattern.

The spatial structure of the surface of the brain determined by a recording can be displayed optically, together with a display of the simulated area of stimulation for the current position of the induction device. With the aid of such an optical display, an operator can alter the position and size of the area of stimulation. For example, by inclining the induction device sideways and/or by moving the induction device towards or away from the head, an as small as possible focus point can be aimed for in order to obtain as high a spatial resolution as possible when localizing particular areas of the brain.

In one embodiment, the induction device can be automatically positioned relative to the head. For example, the induction device can be positioned by a movable robot arm having a number of degrees of freedom, in such a way that a multitude of points on the surface of the brain can be stimulated with as small a focus point as possible. To this end, the movable robot arm can be firmly affixed to the head. In this way, suitable points of stimulation on the surface of the brain can be selected by pattern-recognition software and/or predetermined by an operator, which the robot arm then automatically moves to, such that the positioned induction device stimulates an area of the surface of the brain as possible. For automatic positioning, the simulation model of the induction device and/or of the head can be used.

In one embodiment, the energy used for stimulating can be set automatically, depending on the relative position of the head and the stimulation device.

The energy amount for guiding the induction device for stimulating the particular area of the brain can be set depending on the desired function to be achieved, i.e., depending on whether a particular area of the brain is to be stimulated or suppressed or inhibited. Suitable signal or impulse forms can also then be additionally chosen, which enable a particular area of the brain to be stimulated or inhibited.

In accordance with another aspect of the invention, the invention relates to a method for assigning a stimulation reaction to an area of the brain, where the area of the brain can be stimulated using at least one or a number of stimulation devices which can be arranged adjacently on a plane or on an elliptical or spherical surface and a stimulation reaction being measured by at least one sensor. Such a sensor can include a sensor for measuring a muscle irritation or twitch, arranged on a particular area of a body. One or more sensors can be arranged on one or more finger pads, an arm, a leg and/or a foot, in order to determine whether stimulating one or more areas of the brain causes one or more reactions at the points of the body in question, for example, a muscle twitch. Such sensors can measure not only whether there is any reaction at all but, in accordance with one embodiment, can also measure the intensity of the stimulation reaction or muscle twitch. This makes it possible to determine whether one or more areas of the brain, stimulated simultaneously or consecutively, cause a rather strong or rather weak stimulation reaction. In one embodiment, one or more measured stimulation reactions can be assigned to the area or areas of the brain stimulated, which make it possible to simply determine and show whether an area of the brain currently being stimulated causes a reaction at a particular area of the body or not. Additionally, the intensity of the stimulation reaction caused by the stimulation can also be shown. To this end, a particular color can be assigned to a particular intensity of a measured stimulation reaction. For example, weak stimulation reactions can be indicated by coloring the area of the brain currently being stimulated blue in a simulation representation of the brain, mid-strong stimulation reactions can be indicated orange, and strong stimulation reactions can be indicated by coloring the brain representation red, for example, on a screen.

The method just described, for assigning at least one stimulation reaction to at least one area of the brain, can be performed in conjunction with, or independently of, the method steps described above for stimulating a particular area of a brain.

In accordance with another aspect of the invention, the invention relates to a computer program, which performs a method comprising one or more of the steps described above when it is loaded on a computer or is run on a computer. Furthermore, the present invention relates to a program storage medium or computer program product comprising such a program.

In accordance with another aspect of the invention, the invention relates to an apparatus for stimulating one or more areas of the brain. The apparatus can include a stimulation or induction device and a recording device, such as a nuclear spin tomograph, an ultrasound device or a computer tomography device, which can detect the spatial anatomical structure of the head with its individual anatomical layers or structures and/or the spatial structure of the brain. Furthermore, a computational unit can be provided, using which magnetic and/or electrical properties of the anatomical structures of the head and/or the brain can be determined and an energy amount to be supplied to a stimulation or induction device for stimulating a particular predetermined area of the brain can be calculated and set based on the properties determined in this way.

In one embodiment, the apparatus can include a display device for displaying the area on or in the brain, which may be or is stimulated using the induction device. In this embodiment, an operator can recognize, on the basis of the display, whether the desired area can be stimulated or inhibited, respectively, given the current position of the induction device or whether the position of the induction device has to be altered.

In accordance with another aspect of the invention, the invention relates to an apparatus for assigning a stimulation reaction to an area of the brain, which includes least one stimulation device for stimulating the area of the brain, at least one sensor for measuring a stimulation reaction and at least one computational unit, using which the at least one measured stimulation reaction can be assigned to the at least one stimulated area of the brain. Such an apparatus enables a stimulation reaction measured, for example, by one or more sensors to be directly and automatically assigned to one or more stimulated areas of the brain. This enables an operator to be shown, on a screen showing a simulation model of the brain, whether there is a reaction to the stimulation currently being performed and how strong it is, by suitably coloring the area of the brain currently being stimulated. In this embodiment, it is possible for a stimulation device to be guided over a head and, if stimulation reactions are measured, these can be indicated by coloring a brain model shown on a screen, such that when the stimulation device is suitably moved over the head, larger areas of the brain can gradually be colored in, in order to perform so-called brain mapping. Thus, it is possible to determine which area of the brain has a stronger or weaker influence on a particular part of the body, on which one or more of the reaction sensors described above can be arranged. The position of the stimulated area of the brain determined by the navigation system and/or a simulation of the brain can be used to assign the measured intensity of the stimulation reaction to this position and, for example, to indicate it using various colors.

Furthermore, the invention relates to a system including an apparatus as described above and a stimulation or induction device which, for example, can be a simple coil or a coil in the form of an 8.

In one embodiment, markers can be affixed in a known way to the induction device and/or a head, such that the positional relationship between the induction device and the object or head can be detected in a known way, for example, using cameras, which enables the induction device to be navigated to a position relative to the object or head, which can be advantageous for stimulating a particular area of the brain.

BRIEF DESCRIPTION OF THE DRAWINGS

These and further features of the present invention will be apparent with reference to the following description and drawings, wherein.

DETAILED DESCRIPTION OF THE INVENTION

Figure 1:
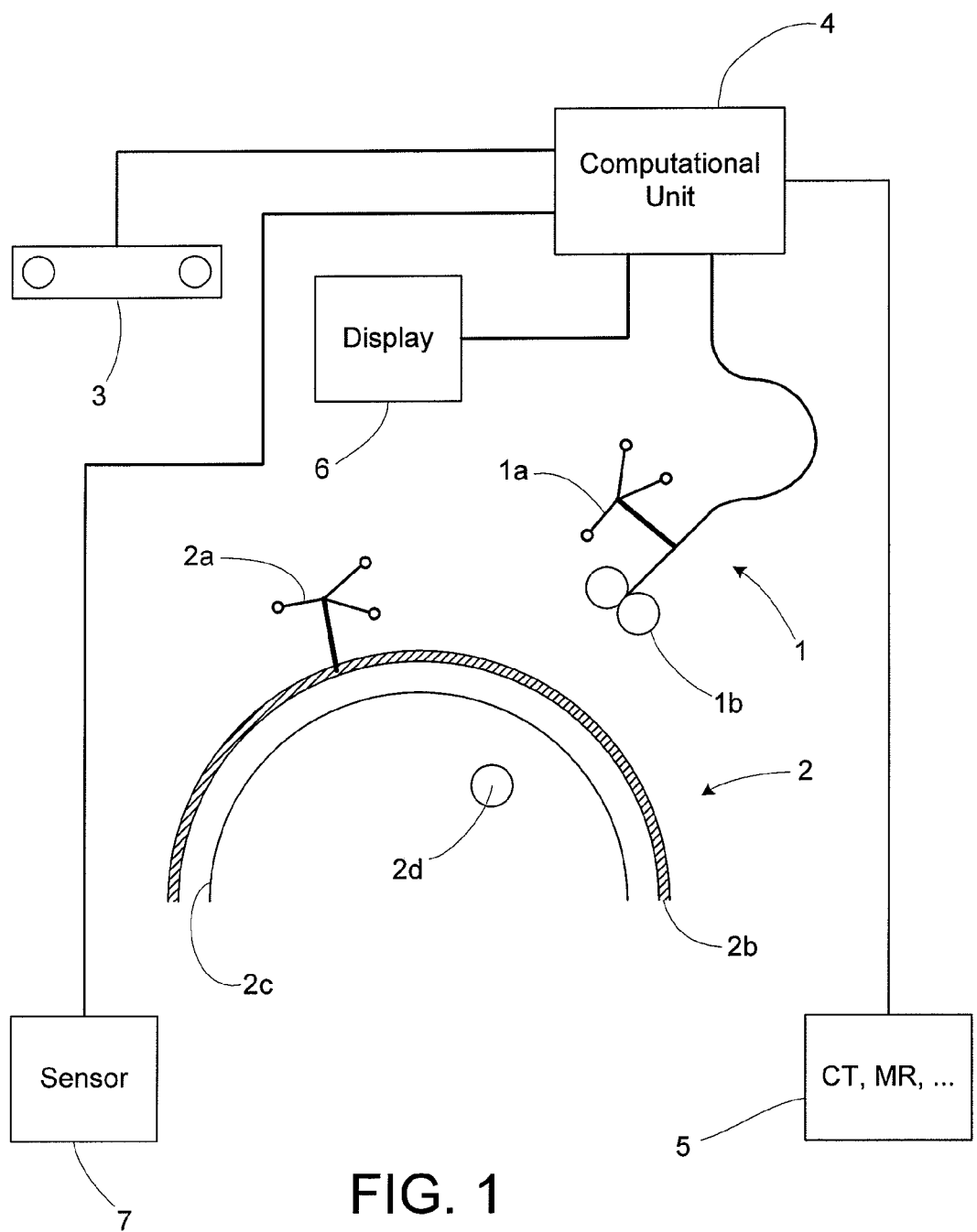
FIG. 1 is a diagrammatic illustration of a system for automatically setting the energy amount to be supplied to an induction device in accordance with the invention.

FIG. 1 is a diagrammatic illustration of a system for automatically setting the energy amount to be supplied to an induction device. FIG. 1 shows a head 2 whose anatomical structure has been determined using a nuclear spin resonance and/or other suitable computer tomography device 5. For example, spatial structures and/or properties of anatomical structures of the head can be determined. These can include, but are not limited to, the course and thickness of the cranium 2b, the quality of the cranium 2b, such as the degree of calcification, the structure, thickness and type of tissue (e.g., scalp and the dura mater), and the position of the brain 2c in the head 2, below the aforementioned anatomical structures. An area 2d to be stimulated by magnetic fields using an induction device 1 is situated on or in the brain 2c. Markers 2a can be arranged on the head 2 in a known way, and can be detected by a camera system 3, such that the spatial position of the head 2 can be determined, using a computational unit 4 connected to the camera system 3, and shown on a display 6.

The computational unit 4 can be connected to the stimulation or induction device 1, on which markers 1a, which can be detected by the camera system 3, are likewise arranged. Thus, the relative position of the stimulation device 1 and the head 2 can be determined. The stimulation device 1 can include a coil 1b (e.g., shaped in the form of an 8) for generating a magnetic field with which the area 2d on the brain 2c can be stimulated.

In one embodiment, an energy amount to stimulate the area 2d as optimally as possible can be set by the computational unit 4 and transferred to the coil 1b of the stimulation device 1. The energy amount can be determined on the basis of the previously determined anatomical structures, or magnetic and/or electrical properties of the head 2 calculated from the same. In addition, the energy amount can be determined using a simulation model of the head 2 and/or a simulation model of the stimulation device 1, and/or a simulation model of the electrical field generated by the stimulation device 1.

The energy amount to be supplied to the coil 1b is can be calculated such that the energy to be supplied to the coil 1b is automatically altered depending on the relative positional relationship of the stimulation device 1 or coil 1b and the head 2, which, for example, enables the coil 1b to be moved over the head 2 and energy to be supplied to the 1b only at positions in which the area 2d of the brain 2c is stimulated.

A sensor 7 can be optionally arranged on an arm of a person being examined, in order to measure the twitch of a particular muscle or some other response. If the area 2d of the brain 2c is stimulated using the induction device 1 and following this stimulation a reaction is measured by the sensor 7, for example in the form of a muscle twitch, then the intensity of the measured reaction can be forwarded to the computational unit 4, which assigns the reaction measured by the sensor 7 to the stimulated area 2d. The intensity of the reaction can be shown on the display 6 on the basis of a simulation model of the brain 2c, where the stimulated area 2d is colored in a particular shade, which can be discretely predetermined and assigned to an intensity, depending on the intensity measured by the sensor 7.

Figure 2:
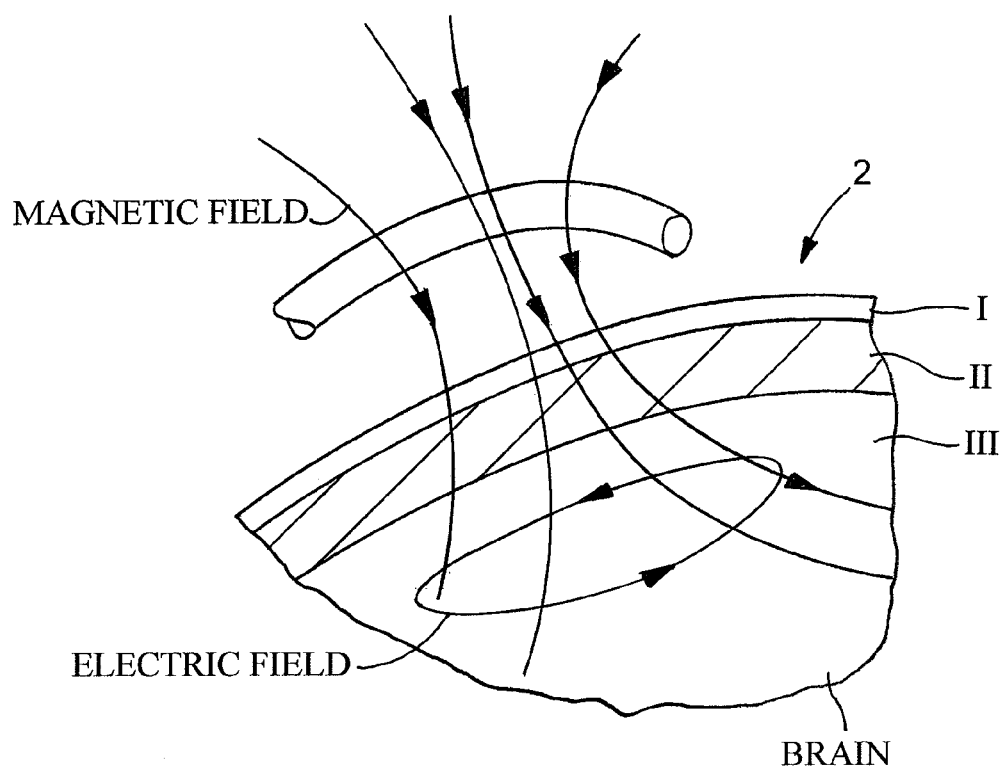
FIG. 2 is a schematic representation of an exemplary simulation model of the head, including three layers.

FIG. 2 schematically shows the course of magnetic and electrical field lines generated by a coil 1b (or portion thereof) lying or otherwise disposed over a head 2. If the anatomical structures and/or properties of the head 2 are known, for example, due to previous recordings, then a simulation model of the head 2 can be produced. The simulation model of the head can include, for example, three shells I, II and III, in order to model the scalp I, the bone structure II and the brain III, as shown schematically in FIG. 2.

Figure 3:
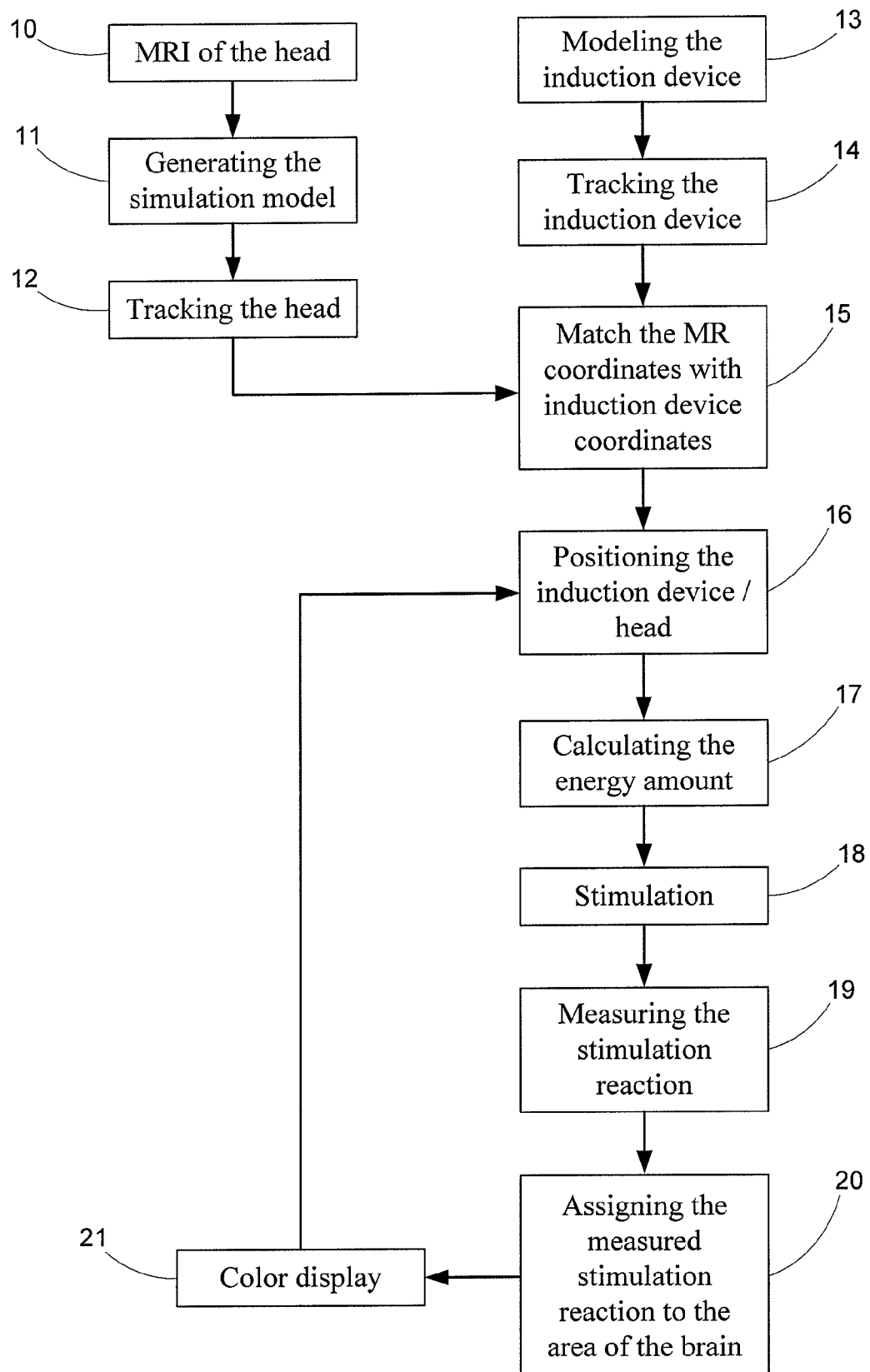
FIG. 3 is a flow chart of a method for automatically setting the energy amount to be supplied to an induction device and stimulating the brain in accordance with the invention.

With reference now to FIG. 3 and continued reference to FIGS. 1 and 2, a flow chart illustrating a method for automatically setting the energy amount to be supplied to an induction device and stimulating the brain in accordance with one embodiment of the present invention is provided. At a first step 10, the spatial structure of a head, together with the brain, can be recorded using nuclear spin resonance (MRI) and computer tomography (CT) or another suitable imaging modality. The data obtained in step 10 can be used in step 11 to generate a simulation model of the recorded head, wherein, as described above, the scalp, the cranium and the brain are modelled as three areas I, II and III, each exhibiting a characteristic dielectric constant and a characteristic conductance. The head can be connected to a reference star 2a or other suitable reference element, as shown in FIG. 1, which enables its spatial position to be simply detected at any time (tracking at step 12).

At step 13, the induction device 1 can be modeled. The modeling can use data obtained from an exact examination of the spatial structure of conductors and/or coils contained in the induction device, such that a magnetic field that can be generated by the induction device can be relatively precisely calculated and simulated. Furthermore, the induction device can also be modeled by evaluating measurements in the magnetic field generated by the induction device. By modeling, a focus range of a concretely used induction device may be relatively precisely defined. As shown in FIG. 1, the induction device 1 can be connected to a reference star 1a or other suitable reference element, which enables the induction device to be tracked (at step 14), just like the head 2 connected to the reference star 2a.

At step 15, the coordinates of the head, and thus of the spatial position of the structure of the brain obtained using MRI and CT, can be aligned or otherwise matched with the co-ordinates of the induction device. This enables the spatial position of the induction device relative to the spatial structure of the head, in particular, of the brain, determined using nuclear spin tomography to be obtained. By using this then known spatial positional relationship, the induction device can be positioned on the head at step 16, wherein the modeling data of the induction device and the modeling data of the head are used to simulate the induction range on the brain, generated when a current flows through the induction device.

If the induction device is positioned such that as small a predetermined area of the brain as possible is stimulated by the induction device during simulation, then the energy amount to be supplied to the induction device can be calculated at step 17, in order to stimulate the predetermined area with the desired intensity. If the energy amount is supplied to the coil of the induction device as current, then the area (determined in advance by simulation) is stimulated at step 18.

After stimulation at step 18, it is optionally possible to measure a stimulation reaction (step 19) and to automatically assign (step 20) the measured stimulation reaction to the area of the brain currently being stimulated and to display (step 21) the intensity of the measured reaction, for example, as a colored indication on a representation of a simulation model of the brain.

An observer can then establish what specific reactions a person shows when this particular area is stimulated. It is possible on the basis of these reactions, such as the twitching of a muscle, disruption to speech or the like, to determine whether the stimulated area of the brain possesses a particular function. If this process of positioning, calculating the energy amount and stimulating is performed for a multitude of areas of the brain by repeating steps 16 to 18, then brain functions can be mapped, wherein the primary areas of the brain of the person being examined can be localized. The induced electrical field desired can be re-calculated again using the simulation models, wherein, for example, up to seven degrees of freedom (three for translation, three for rotation, and one for coil current) can be taken into account with respect to the induction device.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, systems, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for stimulating a particular area of a brain using a stimulation device, said method comprising:
    detecting a spatial structure of a head;
    determining electrical and/or magnetic properties of at least one part of anatomical structures of the head;
    using a computational unit to calculate an energy amount to be provided by the stimulation device for stimulating the particular area of the brain, said calculation being based on the spatial structure of the head and the determined electrical and/or magnetic properties of at least one part of the anatomical structures of the head.

2. The method as set forth in claim 1, wherein determining properties of the anatomical structures includes determining at least one of thickness and type of bones or tissues.

3. The method as set forth in claim 1, further comprising: generating a simulation model of the head from the detected spatial structure of the head.

4. The method as set forth in claim 3, wherein the simulation model is a three-shell model.

5. The method as set forth in claim 3, wherein the simulation model is a multiple-shell model.

6. The method as set forth in claim 1, further comprising:
    arranging reference markers on at least one of the stimulation device and the head; and
    tracking at least one of the stimulation device and the head.

7. The method as set forth in claim 1, wherein the stimulation device includes a coil in the form of an eight.

8. The method as set forth in claim 1, further comprising:
    stimulating areas of the brain using electrical impulses in the stimulation device.

9. The method as set forth in claim 3, further comprising:
    optically displaying the simulated area of stimulation in the brain, said simulated area being determined from the simulation model of at least one of the stimulation device and the head.

10. The method as set forth in claim 1, wherein the stimulation device is automatically positioned relative to the head.

11. The method as set forth in claim 1, wherein the energy supplied to the stimulation device is set depending on the relative position of the stimulation device and the head.

12. The method as set forth in claim 1, wherein the energy to be supplied to the stimulation device is set depending on whether the area of the brain to be stimulated is to be stimulated or blocked.

13. The method as set forth in claim 1, wherein the energy to be supplied to the stimulation device is chosen depending on the area of the brain to be stimulated.

14. A computer-readable medium storing a computer program, wherein when the program is loaded onto a computer and executed, the program causes the computer to carry out the steps of claim 1.

15. The method as set forth in claim 1, wherein the electrical and/or magnetic properties comprise a characteristic dielectric constant and/or a characteristic conductance of at least one part of anatomical structures of the head.

16. A method for assigning a stimulation reaction to an area of the brain, said method comprising:
    stimulating the area of the brain using at least one stimulation device as set forth in claim 1;
    measuring a stimulation reaction; and
    automatically assigning the measured stimulation reaction to the area of the brain.

17. The method as set forth in claim 16, further comprising:
    measuring intensity of the stimulation reaction using at least one sensor.

18. The method as set forth in claim 17, further comprising:
    assigning a predetermined color to the intensity of the measured stimulation reaction; and
    coloring a simulation model of the brain depending on intensity.

19. An apparatus for stimulating a particular area of a brain, said apparatus comprising:
    a device for recording spatial anatomical structures of a head; and
    a computational unit which:
        determines electrical and/or magnetic properties of the anatomical structures of the head; and
        calculates an energy amount for stimulating the particular area of the brain based on the determined electrical and/or magnetic properties of the anatomical structures of the head.

20. The apparatus as set forth in claim 19, further comprising:
    a display device for displaying a stimulated area of the brain or area of the brain to be stimulated.

21. A system comprising the apparatus as set forth in claim 19 and a stimulation device.

22. The system as set forth in claim 21, further comprising:
    markers adapted to be disposed on the stimulation device and/or on the head; and
    a navigation system which determines the relative spatial position of the stimulation device and the head.

* * * * *